US011931725B2

(12) United States Patent
Zhang et al.

(10) Patent No.: US 11,931,725 B2
(45) Date of Patent: Mar. 19, 2024

(54) ETHYLENE OXIDE HIGH SELECTIVITY CATALYST CONDITIONING PROCESS

(71) Applicant: Scientific Design Company, Inc., Little Ferry, NJ (US)

(72) Inventors: Xiankuan Zhang, Houston, TX (US); Christelle Verrier, Little Ferry, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 17/867,950

(22) Filed: Jul. 19, 2022

(65) Prior Publication Data

US 2024/0024857 A1 Jan. 25, 2024

(51) Int. Cl.
| *C07D 301/03* | (2006.01) |
| *B01J 21/04* | (2006.01) |
| *B01J 23/36* | (2006.01) |
| *B01J 23/50* | (2006.01) |
| *B01J 35/00* | (2006.01) |
| *B01J 35/08* | (2006.01) |
| *B82Y 30/00* | (2011.01) |
| *B82Y 40/00* | (2011.01) |

(52) U.S. Cl.
CPC ............... *B01J 23/50* (2013.01); *B01J 21/04* (2013.01); *B01J 23/36* (2013.01); *B01J 35/006* (2013.01); *B01J 35/08* (2013.01); *C07D 301/03* (2013.01); *B82Y 30/00* (2013.01); *B82Y 40/00* (2013.01)

(58) Field of Classification Search
CPC ... B01J 23/50; B01J 21/04; B01J 23/36; B01J 35/006; B01J 35/08; B82Y 30/00; B82Y 40/00; C07D 301/03

USPC .......................................................... 549/256
See application file for complete search history.

(56) References Cited

U.S. PATENT DOCUMENTS

| 3,563,914 A | 2/1971 | Wattimena |
| 3,702,259 A | 11/1972 | Nielsen |
| 3,962,136 A | 6/1976 | Nielsen et al. |
| 4,010,115 A | 3/1977 | Nielsen et al. |
| 4,010,155 A | 3/1977 | Inouye et al. |
| 4,012,425 A | 3/1977 | Nielsen et al. |
| 4,039,561 A | 8/1977 | Mitsuhata et al. |
| 4,066,575 A | 1/1978 | Winnick |

(Continued)

FOREIGN PATENT DOCUMENTS

EP 0352850 A1 1/1990

OTHER PUBLICATIONS

Brunauer, S., et al., "Adsorption of Gases in Multimolecular Layers", J. Am. Chem. Soc., Feb. 1938, pp. 309-316.

(Continued)

*Primary Examiner* — Taylor V Oh
(74) *Attorney, Agent, or Firm* — Scully, Scott, Murphy & Presser, P.C.

(57) ABSTRACT

A conditioning process that is employed with a high selectivity catalyst (HSC) during an initial phase (i.e., start-up) of the epoxidation process is provided. The HSC conditioning process of the present disclosure ensures that the heat release from a catalyst bed containing an HSC during a start-up operation is less than 2000 kJ/Kgcat·hr. The HSC containing catalyst bed that has been conditioned by the process of the present disclosure exhibits improved performance (i.e., EO selectivity) and reduced hot spots.

25 Claims, 5 Drawing Sheets

(56) References Cited

U.S. PATENT DOCUMENTS

| | | | |
|---|---|---|---|
| 4,123,385 | A | 10/1978 | Rebsdat et al. |
| 4,350,616 | A | 9/1982 | Boussert |
| 4,761,394 | A | 8/1988 | Lauritzen |
| 4,766,105 | A | 8/1988 | Lauritzen |
| 4,808,738 | A | 2/1989 | Lauritzen |
| 4,820,675 | A | 4/1989 | Lauritzen |
| 4,833,261 | A | 5/1989 | Lauritzen |
| 4,874,879 | A | 10/1989 | Lauritzen et al. |
| 4,908,343 | A | 3/1990 | Bhasin |
| 5,011,807 | A | 4/1991 | Hayden et al. |
| 5,057,481 | A | 10/1991 | Bhasin |
| 5,099,041 | A | 3/1992 | Hayden et al. |
| 5,102,848 | A | 4/1992 | Soo et al. |
| 5,155,242 | A | 10/1992 | Shankar et al. |
| 5,187,140 | A | 2/1993 | Thorsteinson et al. |
| 5,407,888 | A | 4/1995 | Herzog et al. |
| 7,102,022 | B2 | 9/2006 | Evans et al. |
| 2004/0049061 | A1* | 3/2004 | Lockemeyer ............ B01J 37/14 502/317 |

OTHER PUBLICATIONS

International Search Report and Written Opinion dated Sep. 1, 2023 received in a corresponding foreign application, 9 pages.

* cited by examiner

ETHYLENE OXIDE HIGH SELECTIVITY CATALYST CONDITIONING PROCESS

FIELD OF THE DISCLOSURE

The present disclosure relates to the epoxidation of an olefin, specifically ethylene, to an olefin oxide, especially ethylene oxide (EO), in which a high selectivity catalyst (HSC) is employed. More particularly, the present disclosure relates to a conditioning process that can be employed with an HSC during an initial phase (i.e., start-up) of an epoxidation process.

BACKGROUND

The catalytic epoxidation of an olefin in the presence of a silver-based catalyst producing an olefin oxide is well known in the art. Conventional silver-based catalysts have provided an olefin oxide with notoriously low selectivity. To a large extent, the selectivity determines the economical attractiveness of an epoxidation process. For example, one percent improvement in the selectivity of the epoxidation process can reduce the yearly operating costs of a large-scale olefin oxide plant substantially.

As is known to those skilled in the art, an olefin oxide produced by epoxidation using a silver-based catalyst can be reacted with water, an alcohol or an amine to form a 1,2-diol, a 1,2-diol ether, an alkanolamine or other derivatives. For example, ethylene oxide can be reacted with water to form ethylene glycol which product can be used as a component of an antifreeze composition, a solvent or a base material in the production of polyethylene terephthalates. Any improvement in the selectivity of the epoxidation process can also reduce the yearly operating costs in the overall process for the production of these products.

Highly selective silver-based epoxidation catalysts have been developed which extend the selectivity over 90 mole percent. Such highly selective catalysts include a porous refractory support such as alpha alumina, which has on its surface a catalytic amount of silver and at least one promoter that improves the catalyst performance in the epoxidation process.

The use of alkali metals and transition metals as promoters for silver catalysts is well known for the production of ethylene oxide by the selective oxidation of ethylene in the vapor phase; see, for example, U.S. Pat. Nos. 4,010,155, 4,012,425, 4,123,385, 4,066,575, 4,039,561 and 4,350,616. Highly selective catalysts which contain, in addition to silver, selectivity-enhancing promoters such as rhenium, molybdenum, tungsten or nitrate- or nitrite-forming compounds, are discussed in U.S. Pat. Nos. 4,761,394 and 4,766,105. The catalyst can comprise further elements like alkali metals as described in U.S. Pat. Nos. 3,962,136 and 4,010,115.

Over the last two decades, rhenium was described as being effective in improving the selectivity of alkaline metal promoted silver-based catalyst supported by a refractory porous support; see, for example, U.S. Pat. Nos. 4,761,394 and 4,833,261. Further improvement of silver-based catalysts promoted with alkaline metals and rhenium was achieved by the use of sulfur, Mo, W, Cr as is disclosed in U.S. Pat. Nos. 4,766,105, 4,820,675 and 4,808,738.

In using highly selective silver-based epoxidation catalysts as described, a reaction modifier, for example, an organic halide, can be added to the feed for further increasing the selectivity of the process. The use of reaction modifiers is disclosed, for example, in EP0352850A1, U.S. Pat. Nos. 4,761,394 and 4,766,105.

Despite all the advances made in developing HSCs, these catalysts, like their conventional counterparts, still need to be conditioned during an initial operational phase of the epoxidation process. The conditioning of HSCs is required in order to ensure that the optimal reactivity of the catalyst as well as high selectivity are achieved. The conditioning process typically occurs during the start-up of the epoxidation reaction, i.e., prior to obtaining a sufficient amount of olefin oxide product.

The start-up process and hence conditioning of epoxidation catalysts has also been described in the prior art. For example, U.S. Pat. No. 5,155,242 relates to the start-up of an epoxidation process wherein a non-HSC catalyst is subjected to a pre-soak period in the presence of an organic halide at a temperature less than the operating temperature of the reactor. U.S. Pat. No. 4,874,879 relates to the start-up of an epoxidation process wherein an HSC is subjected to a pre-soak period in the presence of an organic halide at a temperature less than the operating temperature of the reactor.

In addition to these disclosures, U.S. Pat. No. 7,102,022 discloses another start-up process for using an HSC. In accordance with this disclosure, the process includes the steps of contacting a catalyst bed comprising a silver-based highly selective epoxidation catalyst, or a precursor of the catalyst comprising the silver in cationic form, with a feed comprising oxygen at a temperature of the catalyst bed above 260° C. for a period of at most 150 hours, and subsequently decreasing the temperature of the catalyst bed to a value of at most 260° C. Another such start-up process is disclosed in U.S. Patent Application Publication No. 2004/0049061 A1 in which a supported highly selective epoxidation catalyst comprising silver in a quantity of at most 0.17 g per m$^2$ surface area of the support is used. In accordance with this publication, the method includes contacting the catalyst, or a precursor of the catalyst comprising the silver in cationic form, with a feed comprising oxygen at a catalyst temperature above 250° C. for a duration of up to 150 hours, and subsequently decreasing the catalyst temperature to a value of at most 250° C.

Despite the numerous HSC conditioning processes described in the prior art, there is still a need for providing an improved conditioning process that can be employed with an HSC.

SUMMARY

The present disclosure provides a conditioning process that is employed with a high selectivity catalyst (HSC) during an initial phase (i.e., start-up) of the epoxidation process. The term "high selectivity catalyst or HSC" denotes a silver-based catalyst that has a selectivity during normal ethylene oxide (EO) production that is greater than 85 mole percent, typically greater than 87 mole percent, and more typically greater than 90 mole percent. Such silver-based catalysts typically include at least a promoting amount of rhenium and one or more other promoters as will be described herein. Notably, the HSC conditioning process of the present disclosure ensures that the heat release from a catalyst bed containing an HSC during a start-up operation is less than 2000 kJ/Kgcat·hr, preferably less than 1750 kJ/Kgcat·hr, and more preferably less than 1500 kJ/Kgcat·hr. The HSC containing catalyst bed that has been conditioned by the process of the present disclosure exhibits improved performance (i.e., EO selectivity) during ethylene oxide production. Moreover, the HSC containing catalyst bed conditioned utilizing the conditioning process of present disclosure has reduced hot spots as compared to catalyst beds of HSCs that are conditioned utilizing processes in which the heat release is not controlled as described in the present disclosure.

In one aspect of the present disclosure, an HSC conditioning process to be used during initial start-up of an epoxidation process is provided. In one embodiment, the HSC conditioning process of the present disclosure includes initiating an epoxidation reaction by reacting a feed gas composition containing ethylene and oxygen in the presence of a catalyst bed containing a high selectivity silver-based ethylene oxide catalyst at a first temperature of about 180° C. to about 210° C. After confirmation of EO production from this initial charge, a moderator is added to the feed gas composition at a concentration from about 0.05 ppm to about 2 ppm. After confirming chloride breakthrough, the first temperature is increased to a second temperature of about 240° C. to about 270° C. over a time period of about 6 hours to about 60 hours, and thereafter the second temperature is maintained for a time period of about 50 hours to about 150 hours. In accordance with the present disclosure, and during the increasing the first temperature to the second temperature and the maintaining the second temperature, heat release from the catalyst bed is controlled to be less than 2000 kJ/Kgcat·hr.

In the present disclosure, the heat release of the catalyst bed can be controlled by measuring oxygen consumption and EO selectivity during the start-up process. In some embodiments, the heat release of the catalyst bed can be controlled by maintaining oxygen conversion to less than about 70 mole percent, more preferably less than 60 mole percent, and even more preferably about 50 mole percent.

In some embodiments, the maintaining the oxygen conversion includes controlling the ramp rate between 3°/hr to 5° C./hr from the first temperature to the second temperature, while increasing carbon dioxide in the feed gas composition stream.

In some embodiments, the heat release of the catalyst bed can be controlled by maintaining a selectivity of the high selectivity silver-based ethylene oxide catalyst to greater than, or equal to, 75 mole percent, preferably, greater than, or equal to, 80 mole percent, and even more preferably greater than, or equal to, 85 mole percent.

In one preferred embodiment, the heat release of the catalyst bed can be controlled by maintaining the oxygen conversion to about 50 mole percent, and by maintaining a selectivity of the high selectivity silver-based ethylene oxide catalyst containing bed to greater than, or equal to, 80 mole percent. Note that the oxygen conversion referred to in the present disclosure is the oxygen consumption that is directly related to the heat release, not the oxygen conversion percentage.

In addition to the specific start-up process mentioned above, the present disclosure contemplates embodiments in which the above described controlled heat release of an HSC catalyst bed to a value of less than 2000 kJ/Kgcat·hr can be used in any start-up process that includes initiating an epoxidation reaction using a feed gas composition of ethylene and oxygen, adding a moderator to the feed gas composition, and increasing ethylene oxide production.

DETAILED DESCRIPTION

Figure 1A:
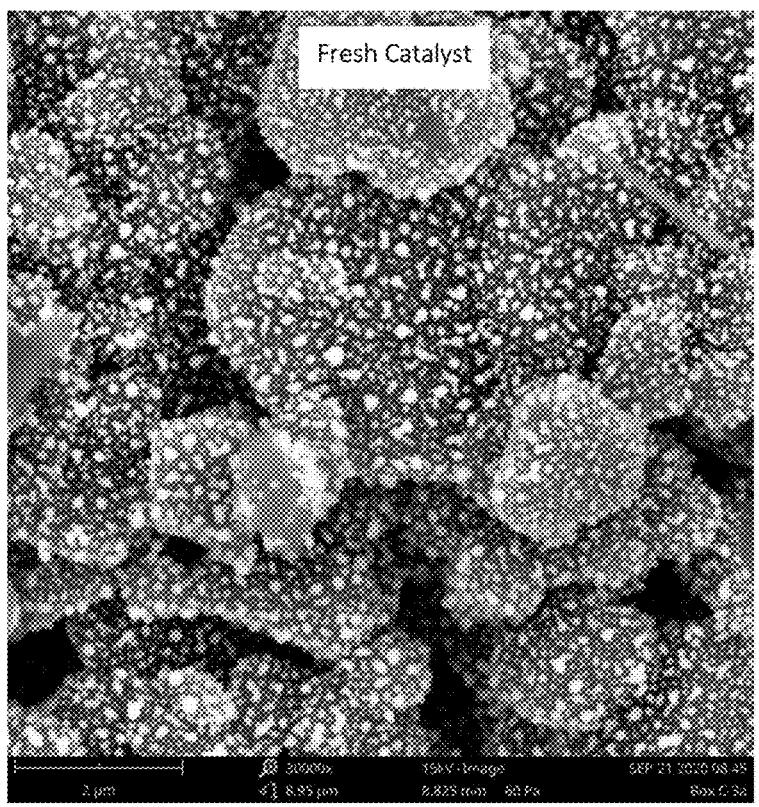
FIG. 1A is a scanning microscope (SEM) image of a fresh HSC prior to performing the conditioning process of the present disclosure.

The present disclosure will now be described in greater detail by referring to the following discussion. In the following discussion, numerous specific details are set forth, such as particular structures, components, materials, dimensions, processing steps and techniques, in order to provide an understanding of the various embodiments of the present disclosure. However, it will be appreciated by one of ordinary skill in the art that the various embodiments of the present disclosure can be practiced without these specific details. As used throughout the present disclosure, the term "about" generally indicates no more than ±10%, ±5%, ±2%, ±1% or ±0.5% from a number. When a range is expressed in the present disclosure as being from one number to another number (e.g., 20 to 40), the present disclose contemplates any numerical value that is within the range (i.e., 22, 24, 26, 28.5, 31, 33.5, 35, 37.7, 39 or 40) or in any amount that is bounded by any of the two values within the range (e.g., 28.5-35).

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising", when used in this disclosure, specify the presence of stated features, integers, steps, operations, elements, and/or components, but do not preclude the presence or addition of one or more other features, integers, steps, operations, elements, components, and/or groups thereof.

As stated above, the present disclosure provides an HSC conditioning process that is employed during start-up of an epoxidation process. The HSC conditioning process of the present disclosure ensures that the heat release from a catalyst bed containing the HSC during the start-up operation is less than 2000 kJ/Kgcat·hr. In the present disclosure, heat release of the catalyst bed is calculated from the oxygen conversion, the catalyst selectivity and the gas hourly space velocity of the reaction. Prior to discussing this HSC conditioning process in detail, a description of the HSC that can be used is provided. The HSC employed in the present disclosure is any silver-based support catalyst which achieves a selectivity during normal ethylene oxide production that is greater than 85 mole percent, preferably greater than 87 mole percent, more preferably, greater than 90 mole percent. The HSC includes a support (i.e., catalyst carrier). The support can be selected from a large number of solid, refractory supports that can be porous. The support can comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. One preferred support is composed of alpha-alumina having a high purity; i.e., at least 95 wt. % pure, or more preferably, at least 98 wt. % alpha-alumina. The remaining components can include inorganic oxides other than alpha-alumina, such as silica, alkali metal oxides (e.g., sodium oxide) and trace amounts of other metal-containing or non-metal-containing additives or impurities.

The support is preferably porous and has a B.E.T. surface area of at most 20 $m^2/g$, preferably from 0.1 to 10 $m^2/g$, and more preferably from 0.5 to 5 $m^2/g$. As used herein, the B.E.T. surface area is deemed to have been measured by the method as described in Brunauer, Emmet and Teller in J. Am. Chem. Soc. 60 (1938) 309-316. The support can have a mono-modal pore size distribution or a multi-modal pore size distribution. Regardless of the character of the support used, it is usually shaped into particles, chunks, pieces, pellets, rings, spheres, wagon wheels, cross-partitioned hollow cylinders, and the like, of a size suitable for employment in fixed-bed epoxidation reactors. Desirably, the support particles can have equivalent diameters in the range of from about 3 mm to about 12 mm and preferably in the range of from about 5 mm to about 10 mm, which are usually compatible with the internal diameter of the tubular reactors in which the catalyst is placed. Equivalent diameter is the diameter of a sphere having the same external surface (i.e., neglecting surface within the pores of the particle) to volume ratio as the support particles being employed.

In order to produce a catalyst for the oxidation of ethylene to ethylene oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used. After impregnation, the excess solution is removed from the impregnated support, and the impregnated support is heated to evaporate the solvent and to deposit the silver or silver compound on the support as is known in the art. Preferred HSCs prepared in accordance with this disclosure contain up to about 45% by weight of silver, expressed as metal, based on the total weight of the catalyst including the support. The silver is deposited upon the surface and throughout the pores of a porous refractory support. Silver contents, expressed as metal, of from about 1% to about 40% based on the total weight of the catalyst are preferred, while silver contents of from about 8% to about 35% are more preferred. The amount of silver deposited on the support or present on the support is that amount, which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide. Useful silver containing compounds which are silver precursors non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

Also deposited on the support, either prior to, coincidentally with, or subsequent to the deposition of the silver is a promoting amount of a rhenium component, which can be a rhenium-containing compound or a rhenium-containing complex. The rhenium promoter can be present in an amount of from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Also deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which can be in the form of metal ions, metal compounds, metal complexes and/or metal salts dissolved in an appropriate solvent. The support can be impregnated at the same time or in separate steps with the various catalyst promoters. The particular combination of silver, support, alkali metal promoters, rhenium component, and optional additional promoters of the instant disclosure will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties can be enhanced by the "promoting amount" while other catalytic properties can or cannot be enhanced or can even be diminished. It is further understood that different catalytic properties can be enhanced at different operating conditions. For example, a catalyst having enhanced selectivity at one set of operating conditions can be operated at a different set of conditions wherein the improvement shows up in the activity rather than the selectivity. In the epoxidation process, it can be desirable to intentionally change the operating conditions to take advantage of certain catalytic properties even at the expense of other catalytic properties. The preferred operating conditions will depend upon, among other factors, feedstock costs, energy costs, by-product removal costs and the like.

Suitable alkali metal promoters can be selected from lithium, sodium, potassium, rubidium, cesium or combinations thereof, with cesium being preferred in some embodiments, and combinations of cesium with other alkali metals, such as lithium, being especially preferred in other embodiment. The amount of alkali metal deposited or present on the support is to be a promoting amount. Preferably, the amount will range from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which can be beryllium, magnesium, calcium, strontium, and barium or combinations thereof. Suitable transition metal promoters can comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter can typically be present in an amount of from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst can further comprise a promoting amount of one or more sulfur compounds, one or more phosphorus compounds, one or more boron compounds, one or more halogen-containing compounds, or combinations thereof. In one embodiment, the catalyst includes from about 5 to about 200 ppm, preferably from about 10 to about 100 ppm sulfur.

The silver solution used to impregnate the support can also comprise an optional solvent or a complexing/solubilizing agent such as are known in the art. A wide variety of solvents or complexing/solubilizing agents can be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent can be present in the impregnating solution in an amount of from about 0.1 to about 5.0 moles per mole of silver, preferably from about 0.2 to about 4.0 moles, and more preferably from about 0.3 to about 3.0 moles for each mole of silver.

When a solvent is used, it can be an organic solvent or water, and can be polar or substantially or totally non-polar. In general, the solvent should have sufficient solvating power to solubilize the solution components. At the same time, it is preferred that the solvent be chosen to avoid having an undue influence on or interaction with the solvated promoters. Examples of organic solvents include, but are not limited to, alcohols, in particular alkanols; glycols, in particular alkyl glycols; ketones; aldehydes; amines; tetrahydrofuran; nitrobenzene; nitrotoluene; glymes, in particular glyme, diglyme and tetraglyme; and the like. Organic-based solvents which have 1 to about 8 carbon atoms per molecule are preferred. Mixtures of several organic solvents or mixtures of organic solvent(s) with water can be used, provided that such mixed solvents function as desired herein.

The concentration of silver in the impregnating solution is typically in the range of from about 0.1% by weight up to the maximum solubility afforded by the particular solvent/solubilizing agent combination employed. It is generally very suitable to employ solutions containing from 0.5% to about 45% by weight of silver, with concentrations of from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, can be used, depending, in part, on the concentration of the silver component in the solution. Impregnation procedures are described in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, rhenium component, alkali metal component, and the optional other promoters, the impregnated support is calcined for a time sufficient to convert the silver containing compound to an active silver species and to remove the volatile components from the impregnated support to result in a catalyst precursor. The calcination can be accomplished by heating the impregnated support, preferably at a gradual rate, to a temperature in the range of from about 200° to about 600° C., preferably from about 200° to about 500° C., and more preferably from about 200 to about 450° C., at a pressure in the range of from 0.5 to 35 bar. In general, the higher the temperature, the shorter the required heating period. A wide range of heating periods have been suggested in the art; e.g., U.S. Pat. No. 3,563,914 suggests heating for less than 300 seconds, and U.S. Pat. No. 3,702,259 discloses heating from 2 to 8 hours at a temperature of from 100° to 375° C., usually for duration of from about 0.5 to about 8 hours. However, it is only important that the heating time be correlated with the temperature such that substantially all of the contained silver is converted to the active silver species. Continuous or step-wise heating can be used for this purpose.

During calcination, the impregnated support can be exposed to a gas atmosphere comprising an inert gas or a mixture of an inert gas with from about 10 ppm to 21% by volume of an oxygen-containing oxidizing component. For purposes of this disclosure, an inert gas is defined as a gas that does not substantially react with the catalyst or catalyst precursor under the conditions chosen for the calcination. Non-limiting examples include nitrogen, argon, krypton, helium, and combinations thereof, with the preferred inert gas being nitrogen. Non-limiting examples of the oxygen-containing oxidizing component include molecular oxygen ($O_2$), NO, $NO_2$, $N_2O$, $N_2O_3$, $N_2O_4$, or $N_2O_5$, or a substance capable of forming NO, $NO_2$, $N_2O$, $N_2O_3$, $N_2O_4$, or $N_2O_5$ under the calcination conditions, or combinations thereof, and optionally comprising $SO_3$, $SO_2$, trimethyl phosphite or combinations thereof. Of these, molecular oxygen is a useful embodiment, and a combination of $O_2$ with NO or $NO_2$ is another useful embodiment. In a useful embodiment, the atmosphere comprises from about 10 ppm to about 1% by volume of an oxygen-containing oxidizing component. In another useful embodiment, the atmosphere comprises from about 50 ppm to about 500 ppm of an oxygen-containing oxidizing component.

After calcining the HSC, the HSC is loaded into reactor tubes of an epoxidation reactor utilizing conventional loading methods well known to those skilled in the art to provide a catalyst bed containing the HSC. The catalyst bed can have packing densities that are suitable for the size of the reactor tubes that are being used. After loading the HSC into the reactor tubes, an inert gas such as nitrogen, can be swept over the catalyst bed to remove any unwanted contaminate from the surface of packed HSC containing catalyst bed.

The HSC containing catalyst bed is thereafter first heated to a first temperature of about 180° C. to about 210° C., which is sufficient to initiate an epoxidation reaction, while pressurizing the recycle loop to the ethylene oxide reactor with a feed gas composition containing ethylene, oxygen and a suitable ballast gas such as methane or nitrogen. The oxygen and ethylene are initially present in small concentrations, such as about 1% to about 4% ethylene and about 0.3% to 0.5% oxygen. After confirming the initiation of ethylene oxide production, a moderator is typically added to the feed gas composition at a concentration of about 0.05 ppm to about 10 ppm, preferably about 0.5 ppm to about 5 ppm; All concentrations recited in this paragraph are by volume. The concentration of the moderator is typically maintained until a time in which chloride is observed in the outlet stream. In some embodiments, chloride can be observed in the outlet stream in a time period from about 2 hours to about 10 hours after the initiation of moderator addition. At that time, which can be referred to a chloride breakthrough, the concentration of moderator is typically lowered to a value that is less than the initial moderator concentration that was added to the feed gas composition. In one embodiment, the moderator is lowered from about 30 percent to about 50 percent below its initial value.

After chlorine breakthrough has been observed, the temperature (i.e., catalyst bed temperature) is gradually increased from the first temperature to a second temperature of about 240° C. to about 270° C., preferably about 260° C. over a period of about 6 hours to about 60 hours. As the catalyst bed temperature is increased, the levels of ethylene and oxygen in the feed are also increased to boost the production level of ethylene oxide, as measured by ΔEO in the reactor effluent, to greater than about 0.6%, preferably greater than about 1.5%. Accordingly during this stage of the start-up process, the feed gas composition will contain about 4% to about 20% of ethylene and about 3% to about 5% oxygen. In some embodiments, the chloride levels are maintained at the same levels as in the previous step. In other embodiments and if the activity is too high, the chloride levels are adjusted to facilitate this temperature increase.

After reaching the second temperature, the temperature is maintained or held for a time period of about 50 hours to about 150 hours—during which time the ethylene and oxygen concentrations in the feed gas are further increased until ethylene oxide production levels comparable to full production levels are reached, during which the ΔEO is greater than about 1.5%, preferably greater than about 2.5%, more preferably in the range of 1.5%-4.0%. At this point the ethylene and oxygen levels will be near or at final operating conditions and the ethylene oxide production levels comparable to full production levels at the completion of this step, the epoxidation process will then continue to operate at these conditions.

During the increasing from the first temperature to the second temperature and the maintaining of the second temperature (i.e., the conditioning stage), heat release of the catalyst bed containing the high selectivity silver-based ethylene oxide catalyst is controlled to be less than 2000 kJ/Kgcat·hr, preferably less than 1750 kJ/Kgcat·hr, and more preferably less than 1500 kJ/Kgcat·hr. It has been determined that HSC conditioned by controlling the heat release exhibit improved EO performance. In the present disclosure, the oxygen consumption and EO selectivity determine the heat release. During the conditioning stage the temperature of the catalyst bed should not exceed 270° C. Typically, and during the conditioning stage, the temperature of the catalyst bed is typically from about 240° C. to less than 270° C. Also, and during the conditioning stage, the oxygen in the outlet stream should not be zero, zero oxygen in the outlet stream typically indicates a runaway reaction.

The heat release by the catalyst bed can be calculated by the total oxygen consumption and EO selectivity. The thermal profile in the catalyst bed should be controlled to be as smooth as possible such that there is a minimal change in temperature (less than 10° C.) across the entire length of the catalyst bed during the conditioning process.

In one embodiment of the present disclosure, the heat release of the catalyst bed is controlled by maintaining oxygen conversion to less than about 70, preferably less than 60, and more preferably 50, mole percent. Once the oxygen conversion has been controlled to a value of less than about 70 mole percent, the reaction conditions that achieve this oxygen conversion should be held substantially constant within the conditioning period. Adjustments can however be used if the oxygen conversion during this conditioning phase exceeds 70 mole percent. In accordance with the present application and to reduce the exotherm in the first tier of the EO reactor, the oxygen conversion should not exceed 70 mole percent. The percentage oxygen conversion is related to the heat release. However, the most important factor is the total oxygen consumption, not the percentage oxygen conversion. When the oxygen concentration is very low (i.e., 1%) in the feed, the percentage oxygen conversion can be high (i.e., up to 80%). If the oxygen concentration in the feed is high (i.e., 5%), the percentage conversation needs to be controlled. In some embodiments of the present disclosure, oxygen conversion ($\Delta O_2$) can be measured by the following formula $\Delta O_2=(O_{2\text{-}inlet}-O_{2\text{-}outlet}/O_{2\text{-}inlet})\times 100\%$ wherein $O_{2\text{-}inlet}$ is the amount of oxygen in mole percent present in the inlet feed gas stream and $O_{2\text{-}outlet}$ is the amount of oxygen in mole percent in the outlet gas stream. In other embodiments, the shrinkage and water factors are also taken into account when calculating the $\Delta O_2$.

In embodiments, the maintaining oxygen conversion includes increasing a ramp rate from the first temperature to the second temperature, while increasing carbon dioxide in the feed gas composition. The increasing of the carbon dioxide concentration in the feed gas composition can occur during the step of increasing from the first temperature to the second temperature, or during the step of maintaining the second temperature or during both of these steps. Typically, the increasing of the carbon dioxide concentration of the feed gas composition occurs prior and during the step of increasing the temperature. The carbon dioxide concentration is then decreased as the selectivity is developing to maintain a steady heat release. In embodiments, the ramp rate can be increased to a rate from about 1° C./hr to about 10° C./hr, preferably a rate from about 2° C./hr to about 8° C./hr, and more preferably, from about 3° C./hr to about 5° C./hr. The carbon dioxide in the feed gas composition can be increased to a value of from about 1 mole percent to about 25 mole percent, and more preferably from a value of about 2 mole percent to about 15 mole percent.

In embodiments, the heat release of the catalyst bed is controlled by maintaining a selectivity of the HSC to greater than, or equal to, 70 mole percent, preferably greater than, or equal to, 80 mole percent, and even more preferably greater than, or equal to, 85 mole percent. In embodiments of the present disclosure, the maintaining the selectivity of the HSC to a value that is greater than, or equal to, 75 mole percent is preferred. In some embodiments, the maintaining the selectivity can include adjusting the moderator concentration during the maintaining phase. The adjusting the moderator concentration can include increasing and/or decreasing the moderator concentration depending on the observed selectivity. Heat release is calculated with oxygen consumption and EO selectivity. To control the heat release one can either decrease the EO production (which is not desirable) or increase the EO selectivity. To increase the EO selectivity, one can adjust the feeds concentrations ($C_2H_4$ and $O_2$ which is not always desirable or possible) or adjust the chlorides concentration. Adjusting the chlorides concentration gives one more flexibility. Increasing or decreasing the chlorides concentration will depends on the activity of the catalyst.

In some embodiments, the heat release of the catalyst bed is controlled by maintaining oxygen conversion to about 50 mole percent, and by maintaining a selectivity of the high selectivity silver-based ethylene oxide catalyst to greater than, or equal to, 78 mole percent.

After performing the conditioning process of the present application, an epoxidation process can be carried out by continuously contacting an oxygen-containing gas with an olefin, which is preferably ethylene, in the presence of an HSC as mentioned above. After the maintaining the second temperature, the high selectivity silver-based catalyst has substantially roundish silver particles having a diameter from about 75 nm to about 500 nm, with a diameter from about 100 nm to about 300 nm being more typical. By "substantially round" it is meant the average circularity of the silver particles is at least 0.80.

Figure 1B:
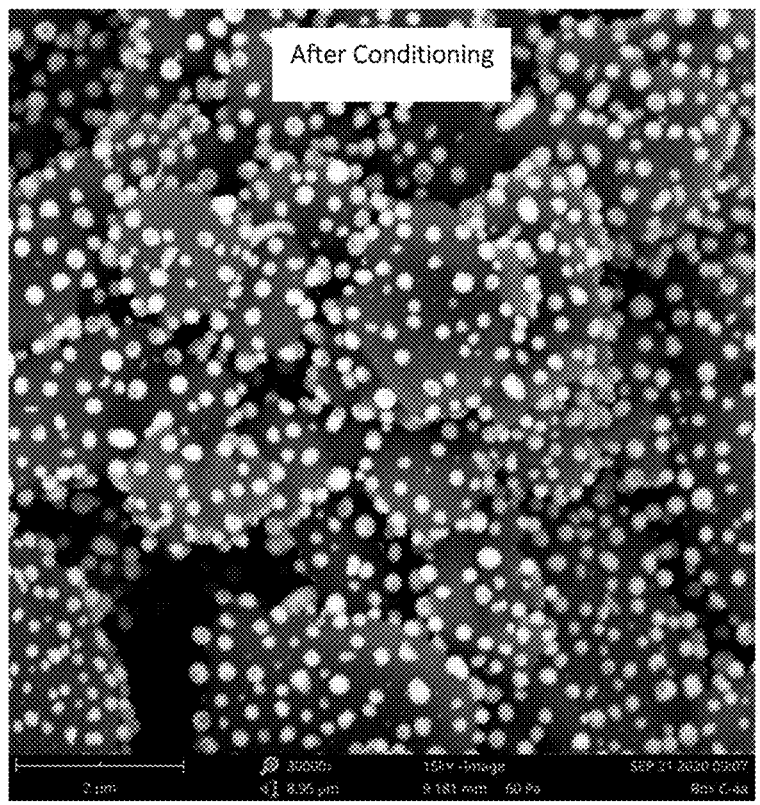
FIG. 1B is a scanning microscope (SEM) image of the fresh HSC shown in FIG. 1A after performing the conditioning process of the present disclosure.
Figure 2A:
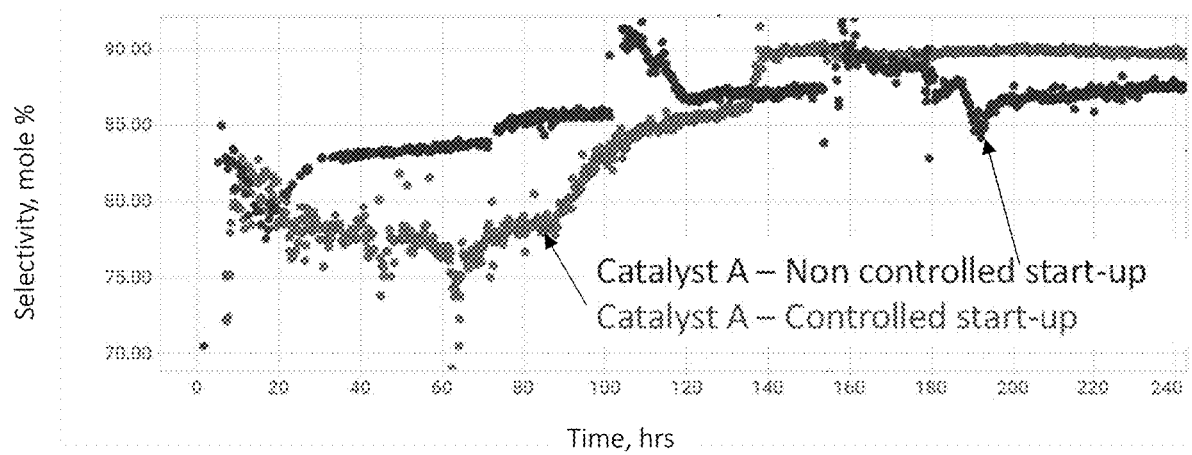
FIG. 2A is a plot of selectivity (mole percent) versus reactor time (hrs) for HSC A using a non-controlled start-up process (not of the disclosure) and a controlled start-up process (of the disclosure).
Figure 2B:
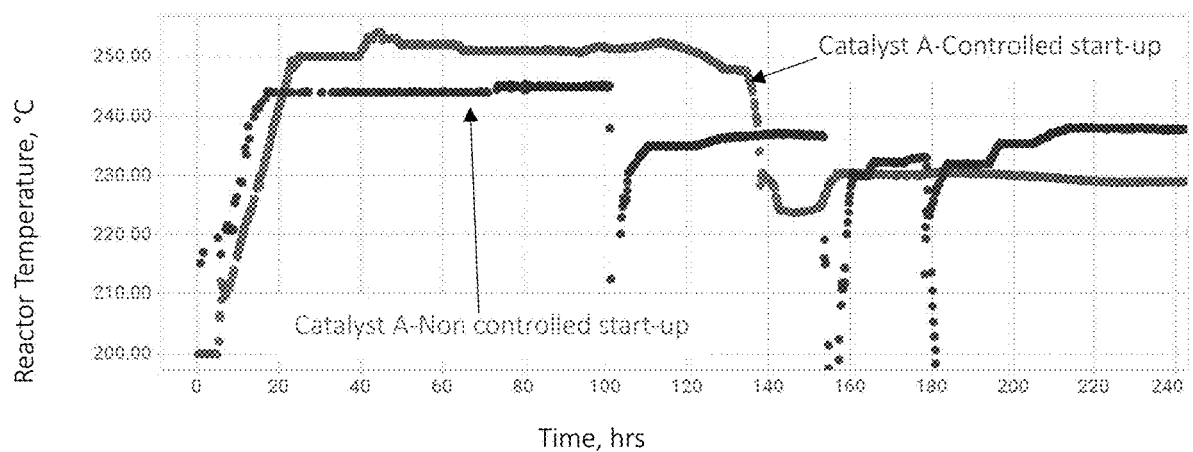
FIG. 2B is a plot of temperature (° C.) versus reactor time (hrs) for HSC A using a non-controlled start-up process (not of the disclosure) and a controlled start-up process (of the disclosure).
Figure 2C:
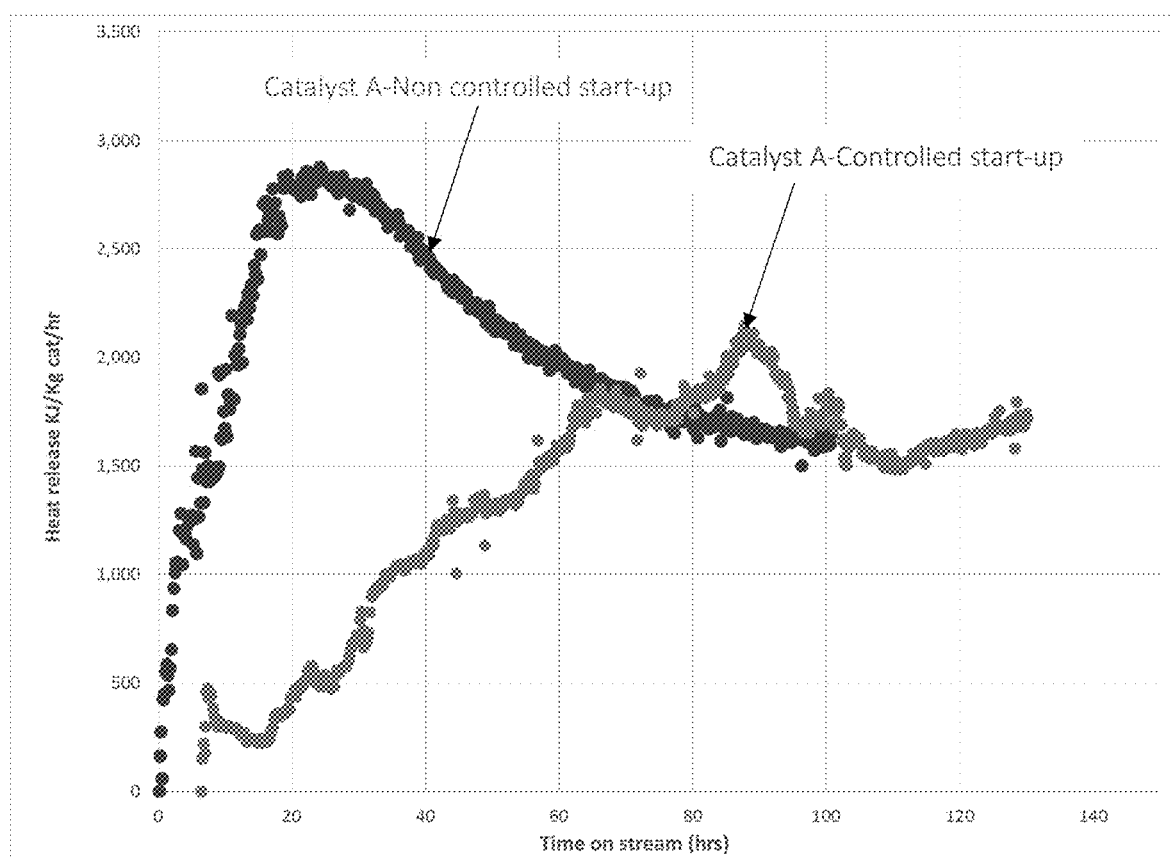
FIG. 2C is a plot of heat release (kJ/Kgcat/hr) versus time on stream (hrs) for HSC A using a non-controlled start-up process (not of the disclosure) and a controlled start-up process (of the disclosure); note that the unit kJ/Kgcat/hr of heat release expressed in the drawing is equivalent to the unit kJ/Kgcat·hr of heat release expressed throughout the disclosure.
Figure 3A:
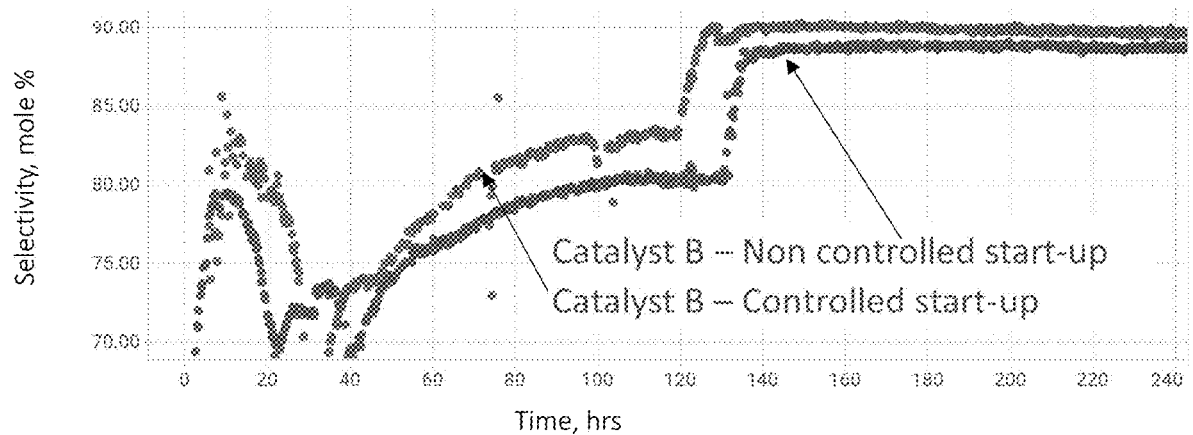
FIG. 3A is a plot of selectivity (mole percent) versus reactor time (hrs) for HSC B using a non-controlled start-up process (not of the disclosure) and a controlled start-up process (of the disclosure).
Figure 3B:
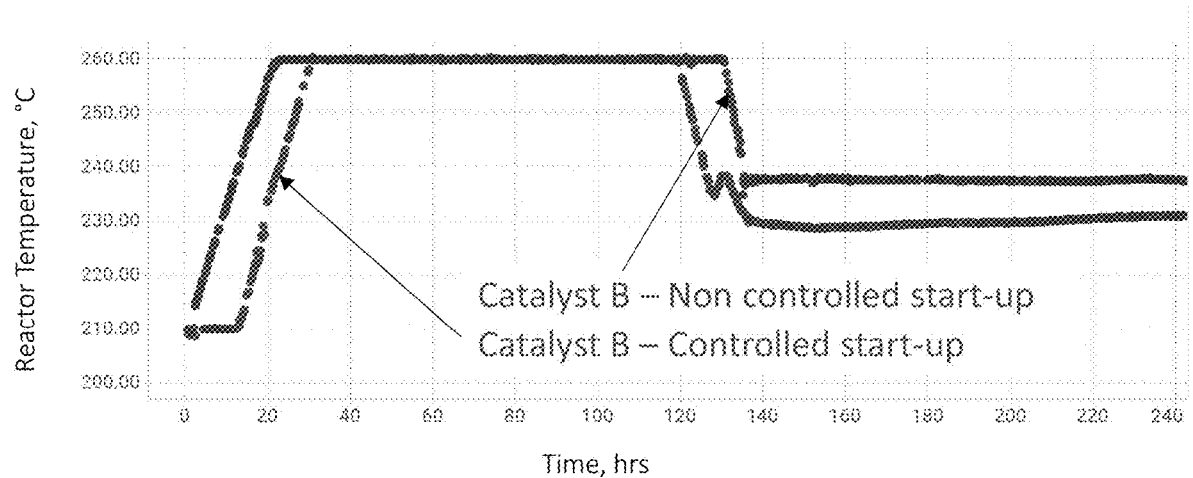
FIG. 3B is a plot of temperature (° C.) versus reactor time (hrs) for HSC B using a non-controlled start-up process (not of the disclosure) and a controlled start-up process (of the disclosure).
Figure 3C:
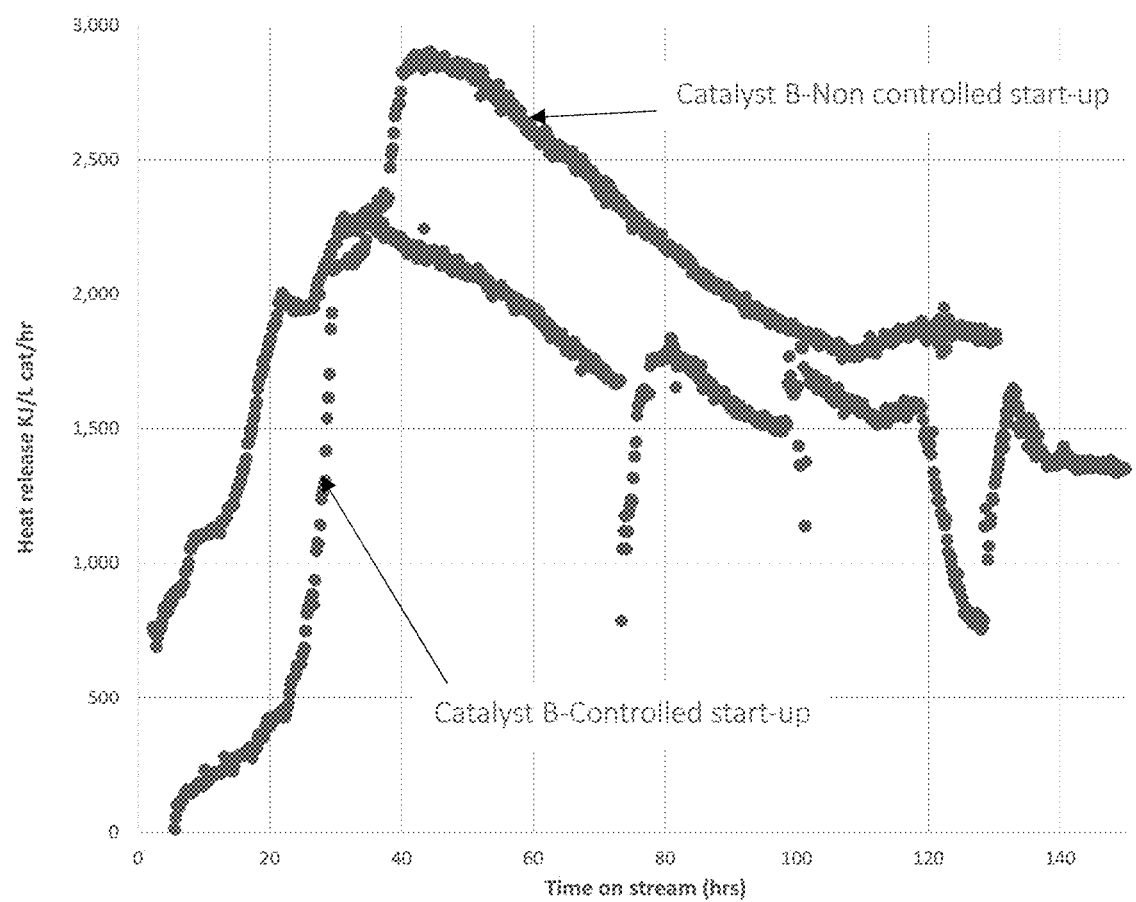
FIG. 3C is a plot of heat release (kJ/Kgcat/hr) versus time on stream (hrs) for HSC A using a non-controlled start-up process (not of the disclosure) and a controlled start-up process (of the disclosure); note that the unit kJ/Kgcat/hr of heat release expressed in the drawing is equivalent to the unit kJ/Kgcat·hr of heat release expressed throughout the disclosure.

Referring first to FIG. 1A, there are shown a fresh HSC prior to performing the conditioning process of the present disclosure. The fresh HSC shown in FIG. 1A has irregular shaped silver particles that have a particle size diameter of less than 75 nm. FIG. 1B shows the fresh HSC shown in FIG. 1A after performing the conditioning process of the present disclosure. The conditioned HSC shown in FIG. 1B have silver particles that are substantially round and these roundish silver particles of the conditioned HSC have a diameter (i.e., particle diameter) of about 100 nm to about 300 nm.

An HSC containing catalyst bed that has been conditioned by the process of the present disclosure described above exhibits improved performance (i.e., EO selectivity) and reduced hot spots as compared to an equivalent HSC containing catalyst bed that has been conditioned without controlling the heat release from the catalyst bed. In one embodiment of the present application, the condition process can provide a 1.1 to 1.3 fold improvement in EO production as compared to an equivalent HSC containing catalyst bed that has been conditioned without controlling the heat release from the catalyst bed. In one embodiment of the present application, the condition process can provide a 0.5-1.5% improvement in EO selectivity as compared to an equivalent HSC containing catalyst bed that has been conditioned without controlling the heat release from the catalyst bed. In one embodiment of the present application, the condition process can provide a reduction in catalyst hot spots as compared to an equivalent HSC containing catalyst bed that has been conditioned without controlling the heat release from the catalyst bed.

In addition to the specific start-up process mentioned above, the present disclosure contemplates embodiments in which the above described controlled heat release of an HSC catalyst bed to a value of less than 2000 kJ/Kgcat·hr can be used in any start-up process that includes initiating an epoxidation reaction using a feed gas composition of ethylene and oxygen, adding a moderator to the feed gas composition, and increasing ethylene oxide production.

Oxygen may be supplied to the reaction in substantially pure molecular form or in a mixture such as air. Molecular oxygen employed as a reactant may be obtained from conventional sources. Reactant feed mixtures may contain from about 0.5% to about 45% ethylene and from about 3% to about 15% oxygen, with the balance (mostly methane) comprising comparatively inert materials including such substances as carbon dioxide, water, inert gases, other hydrocarbons, and one or more reaction modifiers such as organic halides, inorganic halides, nitrogen oxides, phosphorus compounds, sulfur compounds and mixtures thereof. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process. Both have adverse effects on the catalyst performance, so the concentrations of these components are usually kept at a minimum. Non-limiting examples of reaction moderators include organic halides such as $C_1$ to $C_8$ halohydrocarbons. Preferably, the reaction moderator is methyl chloride, ethyl chloride, ethylene dichloride, ethylene dibromide, vinyl chloride or mixtures thereof. Most preferred reaction moderators are ethyl chloride and ethylene dichloride. Usually such reaction moderators are employed in an amount of from about 0.5 to 15 ppmv, preferably from 1 to 8 ppmv of the total volume of the feed gas.

A usual method for the ethylene epoxidation process comprises the vapor-phase oxidation of ethylene with molecular oxygen, in the presence of an HSC, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst and some packing materials at the top and bottom of the tubes. Typical operating conditions for the ethylene epoxidation process involve temperatures in the range of from about 180° to about 330° C., and preferably, about 200° to about 325° C., and more preferably from about 225° to about 270° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 0.3-3 seconds.

The resulting ethylene oxide is separated and recovered from the reaction products using conventional methods. For the present disclosure, the ethylene epoxidation process may include a gas recycle wherein substantially all of the reactor effluent is readmitted to the reactor inlet after substantially or partially removing the ethylene oxide product and the byproducts. In the recycle mode, carbon dioxide concentrations in the gas inlet to the reactor may be, for example, from about 0.1 to 10 volume percent.

The conditioning process of the present application particularly suitable for oxidation of ethylene with molecular oxygen to ethylene oxide. The conditions for carrying out such an oxidation reaction in the presence of the catalysts broadly comprise those described in the prior art. This applies to suitable temperatures, pressures, residence times, diluent materials, moderating agents, and recycle operations, or applying successive conversions in different reactors to increase the yields of ethylene oxide. For purposes of illustration only, the following are conditions that are often used in current commercial ethylene oxide reactor units: a gas hourly space velocity of 1500-10,000 $h^{-1}$, a reactor inlet pressure of 150-400 psig, a coolant temperature of 180-315° C., an oxygen conversion level of 10-60%, and an EO production rate (work rate) of 50-500 kg EO/m³ catalyst·hour. The feed composition at the reactor inlet may typically comprises 1-40% ethylene, 3-12% $O_2$, 0.3-40% $CO_2$, 0-3% ethane, 0.3-20 ppmv total concentration of organic chloride moderator(s), and the balance of the feed being comprised of argon, methane, nitrogen or mixtures thereof.

Examples have been set forth below for the purpose of illustrating the present disclosure. The scope of the present disclosure is not limited to the examples set forth herein Example 1

In this example, a comparison was made between a controlled start-up process in accordance with the present disclosure and a non-controlled start-up process not of the present disclosure both using a same HSC, i.e., HSC A. In both cases the same amount of HSC A was loaded in the tubular reactors and the same target conditions was achieved after conditioning (GHSV=4475 $hr^{-1}$, WR=220 kg EO/m³ catalyst·hour, feed composition ($C_2H_4/O_2/CO_2$=30/8/1 molar ratios) and pressure=300 psig).

The non-controlled conditioning consisted of ramping the temperature to 245° C. coolant temperature (about 255° C. bed temperature) for a set period of time (100 hours total). Carbon dioxide concentration was kept between 1-2 mole percent throughout the conditioning period, while $C_2H_4$ and $O_2$ concentrations were increased progressively during the 100 hours. The heat release exceeded 2700 kJ/Kgcat·hr.

The controlled conditioning consisted of ramping the temperature and $CO_2$ concomitantly until 250-252° C. coolant temperature (about 260-265° C. bed temperature) and 15 mole percent ethylene was obtained. Ethylene and $O_2$ were increased to target concentrations at the same time until the EO production reached 2 mole percent. After EO selectivity exceeded 80 mole percent selectivity the carbon dioxide concentration was decreased. The conditioning was terminated once 1 mole percent $CO_2$ concentration was reached and selectivity stopped increasing. Heat release remained below 2000 kJ/Kgcat·hr at all time.

Example 2

In this example, a comparison was made between a controlled start-up process in accordance with the present disclosure and a non-controlled start-up process not of the present disclosure both using a same HSC, i.e., HSC B. Note HSC B differs from HSC A used in Example 1 above.

In both cases the same amount of HSC B was loaded in the tubular reactors and the same target conditions was achieved after conditioning (GHSV=4475 $hr^{-1}$, WR=220 kg EO/m³ cat·hr, feed composition ($C_2H_4/O_2/CO_2$=30/8/1 molar ratios) and pressure=300 psig).

The non-controlled conditioning consisted of ramping the temperature to 260° C. coolant temperature (about 270-275° C. bed temperature) for a set period of time (100 hours at temperature). Carbon dioxide concentration was kept between 1-2 mole percent throughout the conditioning period while $C_2H_4$ and $O_2$ concentrations were increased progressively during the 100 hours up to 9 mole percent and 5 mole percent respectively. The heat release reached 3000 kJ/Kgcat·hr.

The controlled conditioning consisted of the same protocol, but $CO_2$ concentration was initially increased to 9 mole percent while ramping the temperature. By increasing $CO_2$ the heat release never exceeded 2300 kJ/Kgcat·hr. After EO selectivity exceeded 75 mole percent selectivity the carbon dioxide concentration was decreased down to 1 mole percent.

While the present disclosure has been particularly shown and described with respect to preferred embodiments thereof, it will be understood by those skilled in the art that the foregoing and other changes in forms and details can be made without departing from the spirit and scope of the present application. It is therefore intended that the present application is not limited to the exact forms and details described and illustrated, but fall within the scope of the appended claims.

What is claimed is:

1. A process to be used during initial start-up of an epoxidation process, the process comprising:
   initiating an epoxidation reaction by reacting a feed gas composition containing ethylene and oxygen in the presence of a catalyst bed containing a high selectivity silver-based ethylene oxide catalyst at a first temperature of about 180° C. to about 210° C.;
   adding, after confirmation of ethylene oxide production, to the feed gas composition about 0.05 ppm to 2 ppm of a moderator;
   increasing, after adding the moderator, the first temperature to a second temperature of about 240° C. to about 270° C. over a time period of about 6 hours to about 60 hours; and
   maintaining the second temperature for a time period of about 50 hours to about 150 hour, wherein during the increasing the first temperature to the second temperature and the maintaining the second temperature, heat release from the catalyst bed is controlled to be less than 2000 kJ/Kgcat·hr.

2. The process of claim 1, wherein the heat release of the catalyst bed is controlled by maintaining oxygen conversion to less than about 70 mole percent.

3. The process of claim 2, wherein the oxygen conversion is about 50 mole percent.

4. The process of claim 2, wherein the maintaining the oxygen conversion comprises controlling a ramp rate from the first temperature to the second temperature, while increasing carbon dioxide in the feed gas composition.

5. The process of claim 4, wherein the ramp rate is controlled between 3° C./hr to 5° C./hr, and the carbon dioxide in the feed gas composition is increased to a value of from about 1 mole percent to about 15 mole percent.

6. The process of claim 1, wherein the heat release of the catalyst bed is controlled by maintaining a selectivity of the high selectivity silver-based ethylene oxide catalyst to greater than, or equal to, 70 mole percent.

7. The process of claim 6, wherein the selectivity is greater than, or equal to, 78 mole percent.

8. The process of claim 1, wherein the heat release of the catalyst bed is controlled by maintaining oxygen conversion to about 50 mole percent, and by maintaining a selectivity of the high selectivity silver-based ethylene oxide catalyst to greater than, or equal to, 78 mole percent.

9. The process of claim 1, wherein, after the maintaining the second temperature, the high selectivity silver-based catalyst has substantially round silver particles having a diameter from about 100 nm to about 300 nm.

10. The process of claim 1, wherein the high selectivity silver-based catalyst includes silver in an amount up to 45% by weight.

11. The process of claim 10, wherein the silver is supported on an alpha alumina-containing carrier having a surface area of at most 20 m²/gm.

12. The process of claim 10, wherein the high selectivity silver-based catalyst further comprises a promoting amount of rhenium.

13. The process of claim 12, wherein the promoting amount of rhenium is from about 0.01 wt. % to about 1 wt. %.

14. The process of claim 12, wherein the high selectivity silver-based catalyst further comprises further comprising a promoting amount of at least one alkali metal.

15. The process of claim 14, wherein the at least one alkali metal is a combination of lithium and cesium.

16. The process of claim 14, wherein the high selectivity silver-based catalyst further comprises further comprising a promoting amount of at least one transition metal selected from Mo, W, Cr, Ti, Hf, Zr, V, Ta and Nb.

17. The process of claim 1, wherein the high selectivity silver-based catalyst comprises an alpha aluminum carrier, up to 45 percent by weight silver, and a promoting amount of rhenium, lithium, cesium, tungsten and sulfur.

18. In a start-up process for conditioning of a high selectivity silver-based catalyst that includes initiating an epoxidation reaction using a feed gas composition of ethylene and oxygen, adding a moderator to the feed gas composition, and increasing ethylene oxide production, the improvement comprising:
controlling heat release from a catalyst bed containing the high selectivity silver-based ethylene oxide catalyst to a value of less than 2000 kJ/Kgcat·hr.

19. The start-up process of claim 18, wherein the heat release of the catalyst bed is controlled by maintaining oxygen conversion to less than about 70 mole percent.

20. The start-up process of claim 19, wherein the oxygen conversion is about 50 mole percent.

21. The start-up process of claim 18, wherein the maintaining the oxygen conversion comprises controlling a ramp rate from a first temperature to a second temperature, while increasing carbon dioxide in the feed gas composition.

22. The start-up process of claim 18, wherein the heat release of the catalyst bed is controlled by maintaining a selectivity of the high selectivity silver-based ethylene oxide catalyst to greater than, or equal to, 75 mole percent.

23. The start-up process of claim 22, wherein the selectivity is greater than, or equal to, 80 mole percent.

24. The start-up process of claim 18, wherein the heat release of the catalyst bed is controlled by maintaining the oxygen conversion to about 50 mole percent, and by maintaining a selectivity of the high selectivity silver-based ethylene oxide catalyst to greater than, or equal to, 80 mole percent.

25. The start-up process of claim 18, wherein the high selectivity silver-based catalyst after performing the start-up process has substantially round silver particles having a diameter from about 100 nm to about 300 nm.

* * * * *